United States Patent
Kim et al.

(10) Patent No.: US 10,940,215 B2
(45) Date of Patent: Mar. 9, 2021

(54) ADIPOCYTE-TARGETING NON-VIRAL GENE DELIVERY COMPLEX COMPRISING DUAL PLASMID VECTOR

(71) Applicant: Industry-University Cooperation Foundation Hanyang University, Seoul (KR)

(72) Inventors: Yong-Hee Kim, Seoul (KR); Hyung Jin Kim, Goyang-si (KR); Jee Young Chung, Goyang-si (KR); Yoon Sung Song, Seongnam-si (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 120 days.

(21) Appl. No.: 16/315,346

(22) PCT Filed: Jun. 30, 2017

(86) PCT No.: PCT/KR2017/006963
§ 371 (c)(1),
(2) Date: Jan. 4, 2019

(87) PCT Pub. No.: WO2018/008903
PCT Pub. Date: Jan. 11, 2018

(65) Prior Publication Data
US 2019/0307898 A1 Oct. 10, 2019

(30) Foreign Application Priority Data
Jul. 5, 2016 (KR) .......................... 10-2016-0084631

(51) Int. Cl.
| | |
|---|---|
| *A61K 48/00* | (2006.01) |
| *C07H 21/04* | (2006.01) |
| *A61P 3/04* | (2006.01) |
| *C12N 15/113* | (2010.01) |
| *C12N 15/85* | (2006.01) |

(52) U.S. Cl.
CPC .......... *A61K 48/0025* (2013.01); *A61K 48/00* (2013.01); *A61K 48/0016* (2013.01); *A61P 3/04* (2018.01); *C12N 15/113* (2013.01); *C12N 15/85* (2013.01)

(58) Field of Classification Search
CPC ............ C12N 15/115; C12N 2310/531; C12N 2310/14
See application file for complete search history.

(56) References Cited

U.S. PATENT DOCUMENTS

2006/0122118 A1 6/2006 Ho
2014/0363522 A1* 12/2014 Lengyel ............ A61K 31/4155
424/649

FOREIGN PATENT DOCUMENTS

KR 10-2009-0120948 A 11/2009
KR 10-1447901 B1 10/2014
WO WO 2004/069991 A2 * 8/2004 ........... C12N 15/115

OTHER PUBLICATIONS

Liu et al. (Asian Journal of Andrology, 2012, 14, 536-545).*
Bridge et al. (Nature Genetics, 34, 3, 2003, 263-264).*
Kazuhisa Maeda, et al., "Role of the Fatty Acid Binding Protein mal1 in Obesity and Insulin Resistance", Diabetes, Feb. 2003, pp. 300-307, vol. 52, No. 2.
R. Yang, et al., "RNAi-mediated germline knockdown of FABP4 increases body weight but does not improve the deranged nutrient metabolism of diet-induced obese mice", International Journal of Obesity, 2011, pp. 217-225, vol. 35.
Maria Isabel Queipo-Ortuno, et al., "FABP4 Dynamics in Obesity: Discrepancies in Adipose Tissue and Liver Expression Regarding Circulating Plasma Levels", PLOS One, Nov. 2012, 10 pages, vol. 7, Iss. 11.
International Search Report for PCT/KR2017/006963 dated Sep. 20, 2017 [PCT/ISA/210].

* cited by examiner

Primary Examiner — Amy H Bowman
(74) Attorney, Agent, or Firm — Sughrue Mion, PLLC (57) ABSTRACT

The present disclosure relates to: an adipocyte-targeting non-viral gene delivery complex comprising a sh(FABP4+FABP5) dual plasmid vector; and treatment for obesity and obesity-induced metabolic syndromes by using the same and, more particularly, to a gene delivery complex comprising: an adipocyte-targeting sequence; a nine-arginine (R9) peptide; and a dual plasmid vector comprising a gene for treatment of obesity and obesity-induced metabolic syndromes, wherein the gene for treatment of obesity and obesity-induced metabolic syndromes is a base sequence inhibiting the expression of a FABP4 gene and a FABP5 gene. According to the present disclosure, in order to treat obesity-related diseases, a dual plasmid vector capable of simultaneously inhibiting the FABP4 and FABP5 genes is produced, and this vector is bound to a predetermined delivery system that specifically delivers the vector into adipocytes so as to provide a gene delivery complex. In this way, it is possible to achieve an excellent therapeutic effect on obesity which targets only adipocytes without cytotoxicity.

6 Claims, 8 Drawing Sheets
Specification includes a Sequence Listing.

SEQUENCE LISTING

```
<160> NUMBER OF SEQ ID NOS: 2

<210> SEQ ID NO 1
<211> LENGTH: 6046
<212> TYPE: DNA
<213> ORGANISM: Artificial Sequence
<220> FEATURE:
<223> OTHER INFORMATION: Artificial Vector

<400> SEQUENCE: 1
cctgcaggcg ttacataact tacggtaaat ggcccgcctg gctgaccgcc caacgacccc      60
cgcccattga cgtcaataat gacgtatgtt cccatagtaa cgccaatagg gactttccat     120
tgacgtcaat gggtggagta tttacggtaa actgcccact tggcagtaca tcaagtgtat     180
catatgccaa gtacgccccc tattgacgtc aatgacggta aatggcccgc ctggcattat     240
gcccagtaca tgaccttatg ggactttcct acttggcagt acatctacgt attagtcatc     300
gctattacca tgatgatgcg gttttggcag tacatcaatg ggcgtggata gcggtttgac     360
tcacggggat ttccaagtct ccaccccatt gacgtcaatg ggagtttgtt ttgactagta     420
aatcaacggg actttccaaa atgtcgtaac aactccgccc cattgacgca aatgggcggt     480
aggcgtgtac ggtgggaggt ctatataagc agagctcgtt tagtgaaccg tcagatcagc     540
ttcgaggggc tcgcatctct ccttcacgcg cccgccgccc tacctgaggc cgccatccac     600
gccggttgag tcgcgttctg ccgcctcccg cctgtggtgc ctcctgaact gcgtccgccg     660
```

-continued

```
tctaggtaag tttaaagctc aggtcgagac cgggcctttg tccggcgctc ccttggagcc      720
tacctagact cagccggctc tccacgcttt gcctgaccct gcttgctcaa ctctacgtct      780
ttgtttcgtt ttctgttctg cgccgttaca gatccaagcc accatggttt ctaagggaga     840
agaactcttt actggtgttg tcccaattct ggttgagctg gatggtgatg tgaatggcca      900
caaattctct gtgtctggtg aaggtgaagg agatgcaact tatggaaagc tgactctgaa      960
gttcatttgt acaacaggaa agctgccagt gccttggcca actctggtga ccaccctgac     1020
ttatggtgtt caatgtttca gcagataccc tgaccacatg aagcagcatg acttctttaa     1080
atctgcaatg ccagaaggtt atgttcagga ggacaatc ttctttaagg atgatggaaa       1140
ttataagaca agggcagaag tgaagtttga aggtgataca ctggttaaca gaattgagct     1200
gaaaggcatt gattttaagg aagatggaaa cattctgggt cacaagctgg agtacaacta     1260
taattctcac aatgtttaca ttatggcaga taagcagagg aatggaatta aggctaatttt    1320 caagattaga cacaacattg aggatggatc tgtccaactg gcagaccatt accagcagaa     1380 caccccctatt ggtgatggcc cagttctcct cccagataat cactatctca gcactcaatc    1440
tgctctgtcc aaagacccta atgagaaaag agaccacatg gtcctcctgg agtttgtgac     1500
agcagcagga attactctgg gaatggatga gctgtacaag ggtaagtcac tgactgtcta     1560
tgcctgggaa agggtgggca ggagatgggg cagtgcagga aaagtggcac tatgaaccca     1620
ctagtttgac aattaatcat aagcatagta taatacaact cactatagca attgtactaa     1680
ccttcttctc tttcctctcc tgacaggagg agccatcatg gccaaactca cttctgcagt     1740
cccagtcctc acagcaaggg atgttgcagg ggctgtagag ttctggactg acagattagg     1800
attctccaga gactttgttg aagatgattt tgctggtgtt gtcagagatg atgtcaccct     1860
cttcatctca gcagttcagg accaagttgt ccctgacaac acccttgctt gggtctgggt     1920
cagaggccta gatgagcttt atgcagaatg gtcagaagta gtcagcacaa atttcaggga     1980
tgcctctggc ccagccatga cagaaattgg tgaacaacct gggaaggg aatttgccct      2040 cagagaccct gctggaaatt gtgtccattt tgtagctgag aacaggact aaagctagaa       2100 gctcgctttc ttgctgtcca atttctatta aaggttcctt tgttccctaa gtccaactac     2160
taaactgggg gatattatga agggccttga gcatctggat tctgcctaat aaaaaacatt     2220
tattttcatt gcaatgatgt atttaaatta tttctgaata tttactaaa aagggaatgt     2280 gggaggtcag tgcatttaaa acataaagaa atgaagagct agttcaaacc ttgggaaaat    2340
acactatatc ttaaactcca tgaaagaagg tgaggctgca aacagctaat gcacattggc     2400
aacagcccct gatgcctatg ccttattcat ccctcagaaa aggattcaag tagaggcttg     2460
atttggaggt taaagttttg ctatgctgta ttttaattaa cgttctgcag tatttagcat     2520
gccccaccca tctgcaaggc attctggata gtgtcaaaac agctggaaat caagtctgtt    2580
tatctcaaac tttagcattt tgggaataaa tgatatttgc tatgctggtt aaattagatt    2640
ttagttaaat ttcctgctga agctctagta tgataagtaa cttgacctaa gtgtaaagtt    2700
gagatttcct tcaggtttat atagtcccta tcagtgatag agacctcggt cttcacctga    2760 ggttttcaa aagtagttga caattaatca tcggcatagt atatcggcat agtataatac    2820
gactcactat aggagggcca ccatggtccg tcctgtagaa accccaaccc gtgaaatcaa    2880
aaaactcgac ggcctgtggg cattcagtct ggatcgcgaa aactgtggaa ttgatcagcg    2940
ttggtgggaa agcgcgttac aagaaagccg ggcaattgct gtgccaggca gttttaacga   3000
tcagttcgcc gatgcagata ttcgtaatta tgcgggcaac gtctggtatc agcgcgaagt    3060
```

```
ctttataccg aaaggttggg caggccagcg tatcgtgctg cgtttcgatg cggtcactca    3120
ttacggcaaa gtgtgggtca ataatcagga agtgatggag catcagggcg gctatacgcc    3180
atttgaagcc gatgtcacgc cgtatgttat tgccgggaaa agtgtacgta tcaccgtttg    3240
tgtgaacaac gaactgaact ggcagactat cccgccggga atggtgatta ccgacgaaaa    3300
cggcaagaaa aagcagtctt acttccatga tttctttaac tatgccggaa tccatcgcag    3360
cgtaatgctc tacaccacgc cgaacacctg ggtggacgat atcaccgtgg tgacgcatgt    3420
cgcgcaagac tgtaaccacg cgtctgttga ctggcaggtg gtggccaatg gtgatgtcag    3480
cgttgaactc cgtgatgcgg atcaacaggt ggttgcaact ggacaaggca ctagcgggac    3540
tttgcaagtg gtgaatccgc acctctggca accgggtgaa ggttatctct atgaactgtg    3600
cgtcacagcc aaaagccaga cagagtgtga tatctacccg cttcgcgtcg gcatccggtc    3660
agtggcagtg aagggcgaac agttcctgat taaccacaaa ccgttctact ttactggctt    3720
tggtcgtcat gaagatgcgg acttacgtgg caaaggattc gataacgtgc tgatggtgca    3780
cgaccacgca ttaatggact ggattggggc caactcctac cgtacctcgc attacccta    3840 cgctgaaagag atgctcgact gggcagatga acatggcatc gtggtgattg atgaaactgc    3900
tgctgtcggc tttaacctct ctttaggcat tggtttcgaa gcgggcaaca agccgaaaga    3960
actgtacagc gaagaggcag tcaacgggga aactcagcaa gcgcacttac aggcgattaa    4020
agagctgata gcgcgtgaca aaaccaccc aagcgtggtg atgtggagta ttgccaacga    4080
accggatacc cgtccgcaag gtgcacggga atatttcgcg ccactggcgg aagcaacgcg    4140
taaactcgac ccgacgcgtc cgatcacctg cgtcaatgta atgttctgcg acgctcacac    4200
cgataccatc agcgatctct ttgatgtgct gtgcctgaac cgttattacg gatggtatgt    4260
ccaaagcggc gatttggaaa cggcagagaa ggtactggaa aaagaacttc tggcctggca    4320
ggagaaactg catcagccga ttatcatcac cgaatacggc gtggatacgt tagccgggct    4380
gcactcaatg tacaccgaca tgtggagtga agagtatcag tgtgcatggc tggatatgta    4440
tcaccgcgtc tttgatcgcg tcagcgccgt cgtcggtgaa caggtatgga atttcgccga    4500
ttttgcgacc tcgcaaggca tattgcgcgt tggcggtaac aagaaaggga tcttcactcg    4560
cgaccgcaaa ccgaagtcgg cggcttttct gctgcaaaaa cgctggactg gcatgaactt    4620
cggtgaaaaa ccgcagcagg gaggcaaaca ataatagcta gaggaagact ttttggaaaa    4680
gattaaaaac ccgcttcggc gggttttttt atgcatgtga gcaaaaggcc agcaaaggc    4740 caggaaccgt aaaaaggccg cgttgctggc gttttccat aggctccgcc ccctgacga    4800 gcatcacaaa aatcgacgct caagtcagag gtggcgaaac ccgacaggac tataaagata    4860
ccaggcgttt ccccctggaa gctccctcgt gcgctctcct gttccgaccc tgccgcttac    4920
cggatacctg tccgcctttc tcccttcggg aagcgtggcg ctttctcata gctcacgctg    4980
taggtatctc agttcggtgt aggtcgttcg ctccaagctg ggctgtgtgc acgaaccccc    5040
cgttcagccc gaccgctgcg ccttatccgg taactatcgt cttgagtcca acccggtaag    5100
acacgactta tcgccactgg cagcagccac tggtaacagg attagcagag cgaggtatgt    5160
aggcggtgct acagagttct tgaagtggtg gcctaactac ggctacacta agaacagt    5220 atttggtatc tgcgctctgc tgaagccagt taccttcgga aaaagagttg gtagctcttg    5280
atccggcaaa caaccaccg ctggtagcgg tggtttttt gtttgcaagc agcagattac    5340
gcgcagaaaa aaaggatctc aagaagatcc tttgatcttt tctacggggt ctgacgctca    5400
```

```
gtggaacgaa aactcacgtt aagggatttt ggtcatgttc ttaatcgata ctagtgctgc      5460
agtatttagc atgccccacc catctgcaag gcattctgga tagtgtcaaa acagccggaa      5520
atcaagtccg tttatctcaa actttagcat tttgggaata aatgatattt gctatgctgg      5580
ttaaattaga ttttagttaa atttcctgct gaagctctag tacgataagt aacttgacct      5640
aagtgtaaag ttgagatttc cttcaggttt atatagcttg tgcgccgcct gggtacctga      5700
ggtttttcaa aagtagttga caattaatca tcggcatagt atatcggcat agtataatac      5760
gactcactat aggagggcca ccatggaccc tgttgtgctg caaaggagag actgggagaa      5820
ccctggagtg acccagctca acagactggc tgcccaccct ccctttgcct cttggaggaa      5880
ctctgaggaa gccaggacag acaggcccag ccagcagctc aggtctctca atggagagtg      5940
gaggtttgcc tggttccctg ccctgaagc tgtgcctgag tcttggctgg agtgtgacct      6000
cccagaggct gacactgtgt aaccctaagc ttctagactt aattaa                    6046
```

<210> SEQ ID NO 2
<211> LENGTH: 9
<212> TYPE: PRT
<213> ORGANISM: Artificial Sequence
<220> FEATURE:
<223> OTHER INFORMATION: Synthetic construct

<400> SEQUENCE: 2

```
Cys Lys Gly Gly Arg Ala Lys Asp Cys
1               5
```

ADIPOCYTE-TARGETING NON-VIRAL GENE DELIVERY COMPLEX COMPRISING DUAL PLASMID VECTOR

CROSS REFERENCE TO RELATED APPLICATIONS

This application is a National Stage of International Application No. PCT/KR2017/006963, filed on Jun. 30, 2017, which claims priority from Korean Patent Application No. 10-2016-0084631, filed on Jul. 5, 2016.

TECHNICAL FIELD

The present disclosure relates to an adipocyte-targeting non-viral gene delivery complex comprising a sh(FABP4+FABP5) dual plasmid vector, and treatment for obesity and obesity-induced metabolic syndromes by using the same.

BACKGROUND ART

As an alternative to conventional protein therapies, various gene therapy techniques have been developed, but there are several problems to be solved. One of the problems is that efficient gene influx through a plasma membrane (in an animal cell) and a nuclear membrane has to be achieved with minimal cytotoxicity.

Gene therapy systems can be largely classified into viral vector-mediated systems and non-viral vector-mediated systems. Viral vectors made using a retrovirus, an adenovirus, or the like have an advantage of high transfection efficiency into a cell. However, the viral vectors have inherent problems such as a problem of immunogenicity and genetic recombination, and the like in in vivo use. In order to overcome stability problems of such a viral vector, various polymeric gene delivery systems have been proposed as an alternative to traditional viral vector-based gene delivery methods. However, for polymeric vectors, there is a problem of having intracellular trafficking barriers such as endosomal escape and nuclear localization. Therefore, it is known that viral vectors have problems in terms of immune reaction, self-replication, stability in a body, and the like, and general polymeric vectors exhibit low biocompatibility which results in problems of high cytotoxicity and biotoxicity, and low nucleic acid delivery efficiency.

On the other hand, synthetic peptide-based gene delivery systems cause leakage in endosomal membranes at low pH, and thus lead to DNA condensation, and also promote endosomal escape, so that the above problems associated with polymeric gene delivery systems can be overcome. For this reason, various synthetic peptides have been developed to promote gene delivery in several cell lines in in vitro use. However, the synthetic peptides also have problems such as toxicity and serum instability in in vivo application.

In this regard, research is being conducted on vectors using a short cationic peptide. However, in this case, there is a problem that DNA is unstable in extracellular spaces, and there is also a problem that stability of a complex with DNA, a gene expression level, and the like are insufficient. Furthermore, it is necessary to develop a certain cell-specific gene delivery vector which is capable of increasing a desired gene expression level due to retaining a targeting ability to a specific cell so that influx of DNA into a target cell and liberation of DNA from a complex is facilitated.

Meanwhile, in a case where the target cell is an adipocyte, in particular, a mature obese adipocyte, there is a problem that it is very difficult to cause transfection since such a cell is a finally differentiated cell. Research using electroporation has also been reported for transfection into an adipocyte. However, for the research, it is known that transfection efficiency is merely about 10%. Moreover, for such a method in in vivo gene delivery systems, adipose tissue-selective targeting delivery has not been attempted.

In this regard, the present inventors found that a complex of an adipocyte-targeting sequence (ATS) and a specific peptide sequence binds to prohibitin which is expressed in a mature adipocyte, and thus effectively delivers a gene into the adipocyte. Based on this finding, the present inventors have developed and reported a non-viral adipocyte-targeting gene delivery system (Korean Patent No. 10-1447901). For example, the above document describes a gene delivery complex in which a FABP4 gene that encodes a fatty acid binding protein (FABP) is bound, in the form of shRNA, to a complex of an ATS and a R9 sequence.

In this regard, nine FABP genes have been reported to date. Among these, FABP4 is known to play a key role in the import and storage of fatty acids in adipocytes. Therefore, also in the above-mentioned Patent Document 1, an attempt was made to achieve a therapeutic effect on obesity in such a way that a gene delivery complex containing a shFABP4 gene is produced and then expression of FABP4 in adipocytes is inhibited. However, a sufficient body weight loss effect could not be observed. Therefore, there is a need to develop a technique which is capable of achieving an efficient therapeutic effect on obesity by using a non-viral adipocyte-targeting gene delivery system.

DISCLOSURE

Technical Problem

In order to solve the problems in the related art, in treatment of obesity-related diseases by delivering a gene for treatment of obesity and obesity-induced metabolic syndromes using a gene delivery vehicle that targets adipocytes, the present disclosure is intended to provide an adipocyte-targeting non-viral gene delivery complex comprising a dual plasmid vector which is capable of exerting an excellent therapeutic effect on obesity without cytotoxicity.

Technical Solution

In order to solve the above problems of the present disclosure, there is provided a gene delivery complex which comprises:
an adipocyte-targeting sequence;
a nine-arginine (R9) peptide; and
a dual plasmid vector comprising a gene for treatment of obesity and obesity-induced metabolic syndromes,
wherein the gene for treatment of obesity and obesity-induced metabolic syndromes is a base sequence inhibiting expression of a FABP4 gene and a FABP5 gene.

According to a preferred embodiment of the present disclosure, the base sequence may be DNA or RNAi.

According to another preferred embodiment of the present disclosure, the RNAi may be siRNA or shRNA.

According to still another preferred embodiment of the present disclosure, the dual plasmid vector may have a base sequence represented by SEQ ID NO: 1.

According to yet another preferred embodiment of the present disclosure, a weight ratio of the gene for treatment of obesity and obesity-induced metabolic syndromes to the adipocyte-targeting sequence and the R9 peptide may be 1:1 to 1:4.

According to yet another preferred embodiment of the present disclosure, a weight ratio of the gene for treatment of obesity and obesity-induced metabolic syndromes to the adipocyte-targeting sequence and the R9 peptide may be 1:2.

According to yet another preferred embodiment of the present disclosure, the adipocyte-targeting sequence may have an amino acid sequence represented by SEQ ID NO: 2.

According to yet another preferred embodiment of the present disclosure, the nine-arginine (R9) peptide may have a structure of Cys-(D-R)9-Cys.

According to yet another preferred embodiment of the present disclosure, the adipocyte may be a differentiated mature obese adipocyte.

Advantageous Effects

According to the present disclosure, in order to treat obesity-related diseases, a dual plasmid vector capable of simultaneously inhibiting the FABP4 gene and the FABP5 gene is produced, and this vector is bound to a predetermined delivery vehicle that specifically delivers the vector into adipocytes so as to provide a gene delivery complex. In this way, it is possible to achieve an excellent therapeutic effect on obesity which targets only adipocytes without cytotoxicity.

MODES OF THE INVENTION

Definitions of terms used herein are as follows.

"Gene" refers to any nucleic acid sequence or portion thereof which has a functional role during protein encoding or transcription or during regulation of expression of another gene. The gene may consist of all nucleic acids encoding a functional protein or may consist of only a portion of nucleic acids encoding or expressing a protein. The nucleic acid sequence may contain a genetic abnormality within exons, introns, initiation or termination regions, promoter sequences, other regulatory sequences, or unique sequences adjacent to the gene.

The term "polynucleotide" or "nucleic acid" refers to a nucleotide polymer of any length, including a ribonucleotide as well as a deoxyribonucleotide. This term refers only to a primary structure of a molecule, and thus refers to double- or single-stranded DNA or RNA. This also includes known types of modifications, for example, labels, methylation, "caps", substitution of one or more naturally-occurring nucleotides with an analog, and internucleotide modifications, including those with uncharged linkages (for example, methyl phosphonates, phosphotriesters, phosphoamidates, and carbarnates) and with charged linkages (for example, phosphorothioates and phosphorodithioates), those containing pendant moieties such as proteins (for example, nucleases, toxins, antibodies, signal peptides, and poly-L-lysine), those with intercalators (for example, acridine and psoralen), those with chelates (for example, metal elements, radioactive metal elements, boron, and oxidative metal elements), those with alkylators, those with modified linkages (for example, alpha anomeric nucleic acids), as well as unmodified forms of a polynucleotide, which are known in the art. Generally, nucleic acid moieties provided by the present disclosure will be combined into unique nucleotides which provide a synthetic nucleic acid which is capable of being expressed in a recombinant transcriptional unit that comprises a fragment of a genome, a short oligonucleotide linker or a series of oligonucleotides, and a regulatory element derived from a microbial or viral operon, or a eukaryotic gene.

The term "vector" refers to a nucleic acid molecule capable of transporting another nucleic acid to a place where the other nucleic acid is associated. The term "expression vector" includes a plasmid, cosmid, or phage which is capable of synthesizing a protein encoded by each of recombinant genes to be transported by the vector. A preferred vector is a vector that allows self-replication and expression of an associated nucleic acid.

"Transfection" refers to a method by which a nucleic acid (DNA, PNA, or the like) is directly introduced into a cultured animal cell so that genetic traits are expressed in the cell. In a case where a target is a plant cell, cell walls of the plant cell are often removed and a nucleic acid is introduced into a protoplast. For the nucleic acid to be introduced, it is a general method to place a desired gene in a vehicle such as a plasmid, and to perform introduction. In a case where an introduced gene is stabilized in a cell, the introduced gene is often inserted into a chromosome. A cell into which a nucleic acid has been introduced is called a "transfectant". Due to very low transfection efficiency, several methods have been developed to increase the efficiency. Among these, methods such as calcium phosphate co-precipitation, DEAE-dextran treatment, electroporation, and redistribution (a method of fusing an artificial membrane called a liposome with a cell that produces a DNA complex) are mentioned.

"Amino acid" and "amino acid residue" refer to a natural amino acid, a non-natural amino acid, and a modified amino acid. Unless otherwise stated, all references to amino acids, generally or specifically depending on names, include references to both D- and L-stereoisomers thereof (in a case where structures of the amino acids allow such stereoisomeric forms). Examples of the natural amino acid include alanine (Ala), arginine (Arg), asparagine (Asn), aspartic acid (Asp), cysteine (Cys), glutamine (Gln), glutamic acid (Glu), glycine (Gly), histidine (His), isoleucine (Be), leucine (Leu), lysine (Lys), methionine (Met), phenylalanine (Phe), proline (Pro), serine (Ser), threonine (Thr), tryptophan (Trp), tyrosine (Tyr), and valine (Val). Examples of the non-natural amino acid include modified amino acid residues which are chemically modified, or chemically blocked in a reversible or irreversible manner, on N-terminal amino groups or side chain groups, for example, N-methylated D and L amino acids, or residues whose side chain functional group is chemically modified to another functional group.

"Support, carrier, or delivery vehicle" refers collectively to a polymeric material responsible for transport of a transporter in a case where an active material in an organism is present in the form of being bound to another material, or a material migrates through a cell membrane. Non-limiting examples of the support include buffers such as phosphates, citrates, and other organic acids; antioxidants such as ascorbic acid; proteins such as low molecular weight polypeptides (having less than about 10 residues), serum albumin, gelatin, and immunoglobulins; hydrophilic polymers such as polyvinylpyrrolidone; amino acids such as glycine, glutamine, asparagine, arginine, and lysine; monosaccharides, disaccharides, and other carbohydrates including glucose, mannose, and dextrin; chelating agents such as EDTA; sugar alcohols such as mannitol and sorbitol; salt-forming counterions such as sodium; and/or nonionic surfactants such as TWEEN, polyethylene glycol (PEG), and PLURONICS.

"Treatment" refers to an approach to obtain beneficial or desired results, including clinical results. "Treatment" or "alleviation" of a disease, disorder, or condition means that a degree of state of the disease, disorder, or condition, and/or undesirable clinical symptoms thereof are decreased, and/or a progression trend thereof is slowed or prolonged, as compared with a case where the disease, disorder, or condition is not treated. For example, in treatment of obesity, weight loss, for example, weight loss of at least 5% is an example of a desirable treatment outcome. For purposes of the present disclosure, examples of a beneficial or desired clinical outcome include, but are not limited to, relief or amelioration of one or more symptoms, diminishment of a degree of disease, a stabilized (that is, not worsened) state of disease, delayed or slowed disease progression, amelioration or alleviation of a disease state, and (partial or total) remission, regardless of whether the outcome is detectable or undetectable. The treatment may also mean prolonging survival as compared with expected survival in the absence of treatment. In addition, the treatment does not need to take effect by administration of a single dose, and often takes effect upon administration of a series of doses. Thus, a therapeutically effective amount, an amount sufficient to cause alleviation, or an amount sufficient to treat a disease, disorder, or condition may be administered in one or more administrations.

The term "disorder" is any state that may benefit from treatment with a molecule identified using a transgenic animal model of the present disclosure. This includes chronic and acute diseases or illnesses including pathological conditions that make mammals susceptible to suspected diseases. Examples of illnesses to be dealt with in the present specification include obesity and metabolic syndrome symptoms, but are not limited thereto.

"Therapeutically effective amount" refers to an amount of an active compound in a composition that will elicit a biological or medical response in tissue, a system, a subject, or a human which includes relief of symptoms of a disorder to be treated and is sought by researchers, veterinarians, medical doctors, or other clinicians.

"Prophylactically effective amount" refers to an amount of an active compound in a composition that will elicit a biological or medical response in tissue, a system, a subject, or a human which is sought by researchers, veterinarians, medical doctors, or other clinicians to prevent obesity, or obesity-related disorders, conditions, or diseases from developing in a subject at risk of the obesity, or the obesity-related disorders, conditions, or diseases.

"Gene therapy" refers to treatment of a genetic disease by correcting a mutated gene, or to treatment of an illness by regulating protein expression using a gene or RNAi. That is, the gene therapy is a method for treating an illness by transplanting a normal gene from an outside into a patient's cell so that a phenotype of the cell is changed. Research on gene vectors and systems that bring a gene into a body is essential for the gene therapy.

"About" refers to a quantity, level, value, number, frequency, percentage, dimension, size, amount, weight, or length which varies by as much as 30%, 25%, 20%, 25%, 10%, 9%, 8%, 7%, 6%, 5%, 4%, 3%, 2%, or 1% with respect to a reference quantity, level, value, number, frequency, percentage, dimension, size, amount, weight, or length.

Throughout the present specification, unless the context otherwise requires, the terms "include (comprise)," "includes (comprises)," and "including (comprising)" should be understood to imply the inclusion of a stated step or element or group of steps or elements but not the exclusion of any other step or element or group of steps or elements.

Hereinafter, the present disclosure will be described in more detail.

As described above, the present disclosure is intended to improve unsatisfactory therapeutic effects of conventional therapeutic agents for obesity-related illnesses. In particular, the present disclosure is intended to improve problems of the adipocyte-targeting gene delivery system that had been reported by the present inventors and comprises an ATS sequence, a R9 sequence, and a shFABP4 gene.

In other words, even in a case where expression of FABP4 is decreased in target adipocytes by the adipocyte-targeting gene delivery system, a satisfactory level of therapeutic effects on obesity was not observed. The present inventors have presumed that these results are due to a compensation effect in the target adipocytes.

Specifically, in a case where the shFABP4 gene is delivered into the target adipocytes by the gene delivery system, expression of the FABP4 gene in the target adipocytes is decreased, and thus an amount of FABP4 proteins in the cells is decreased. Therefore, it can be expected that therapeutic effects on obesity are achieved due to a decrease of the FABP4 proteins which play a key role in importing and storing fatty acids into adipocytes. However, in reality, it has been observed that a satisfactory level of therapeutic effects on obesity as expected is not achieved. It was reasoned that this is because an expression level of a FABP5 gene, which plays a key role in induction of obesity together with FABP4, is increased as a compensation mechanism for decreased expression level of the FABP4 gene. Based on the reasoning, the present inventors have found that it is essential to simultaneously decrease expression levels of the FABP4 gene and the FABP5 gene for effectively treating obesity.

Meanwhile, conventional gene delivery systems are gene delivery systems which deliver only one gene. Therefore, in order to simultaneously inhibit two genes, in principle, twice as many gene delivery vehicles are required for the respective genes. However, in a case where an amount of the gene delivery vehicles is increased for delivery of specific genes, there is a problem of causing cytotoxicity. Therefore, in order to solve such a problem, the present disclosure is intended to use a dual plasmid vector. That is, in the present disclosure, two genes to be inhibited are inserted into a single plasmid, so that simultaneous inhibition of the two genes can be achieved in a case where the plasmid is delivered into a cell of interest.

Accordingly, in the present disclosure, there is provided a gene delivery complex, comprising:

an adipocyte-targeting sequence;
a nine-arginine (R9) peptide; and
a dual plasmid vector comprising a gene for treatment of obesity and obesity-induced metabolic syndromes,
wherein the gene for treatment of obesity and obesity-induced metabolic syndromes is a base sequence inhibiting expression of the FABP4 gene and the FABP5 gene.

As can be seen from results of the following examples, in a case where the gene delivery complex according to the present disclosure is used to simultaneously inhibit the FABP4 gene and the FABP5 gene, further superior therapeutic effects on obesity can be achieved as compared with those achieved with single gene inhibition, and inflammation-decreasing effects in obesity tissue can also be achieved.

In the gene delivery complex according to the present disclosure, the adipocyte-targeting sequence (ATS) and the nine-arginine (R9) peptide specifically deliver a therapeutic gene into adipocytes. That is, the gene delivery complex according to the present disclosure is a non-viral gene delivery complex comprising the ATS and a poly(oligo-arginine), in particular, the nine-arginine (R9) peptide, in which the ATS-R9 sequence binds to prohibitin in adipocytes, and thus can specifically deliver the therapeutic gene into the adipocytes.

Among constituent components of the gene delivery complex according to the present disclosure, details related to the ATS and the nine-arginine (R9) peptide are specifically described in Korean Patent Application No. 10-2013-0041402, which is a prior art document by the present inventors, and the content of which is incorporated herein by reference in its entirety.

As the gene for treatment of obesity and obesity-induced metabolic syndromes to be delivered by the complex of the present disclosure, any gene whose expression in a target adipocyte is desired can be inserted, and examples thereof include DNA and RNA, and synthetic analogues thereof. For example, genes which encode polypeptides (enzymes, hormones, growth factors, cytokines, receptors, structural proteins, and the like), antisense RNAs, ribozymes, decoys, and RNAs that cause RNA interference, and the like are exemplified. Specific examples thereof can include gDNA, cDNA, pDNA, mRNA, tRNA, rRNA, siRNA, miRNA, and antagomirs. These genes may be naturally occurring or synthesized, and may exist in various sizes from oligonucleotides to chromosomes. Such genes originate from humans, animals, plants, bacteria, viruses, and the like. Such genes may be acquired using methods known in the art.

Examples of the polypeptides encoded by the genes can include various hormones, histocompatible antigens, cell adhesion proteins, cytokines, various antibodies, cell receptors, endoenzymes or ectoenzymes, and fragments thereof. In addition, examples of the polypeptides can include expression regulatory factors of the gene for treatment of obesity and obesity-induced metabolic syndromes, for example, transcription promoters, enhancers, silencers, operators, terminators, attenuators, other expression regulatory factors, and the like.

In the present disclosure, preferred examples of the gene for treatment of obesity and obesity-induced metabolic syndromes include genes encoding polypeptides associated with treatment or diagnosis of obesity and obesity-induced metabolic syndromes. In particular, the gene for treatment of obesity and obesity-induced metabolic syndromes is preferably RNA interference (RNAi) having gene therapeutic effects on obesity diseases.

The RNA interference (RNAi) is a natural mechanism that involves specifically down-regulating expression of a gene of interest by double-stranded small interfering RNA (siRNA). As examples of types of RNAi reagents that mediate RNAi, for example, siRNA or microRNA (miRNA), or short hairpin RNA (shRNA) are mentioned.

Specifically, as the shRNA, sh(FABP4+FABP5), which is capable of simultaneously inhibiting expression of the FABP4 gene and the FABP5 gene, can be used. Doses and regimes effective for administration of the RNAi can be determined empirically and can be readily determined by those skilled in the art. A single dose or multiple doses may be used.

Meanwhile, a weight ratio of the gene for treatment of obesity and obesity-induced metabolic syndromes to the remaining components constituting the gene delivery complex according to the present disclosure, that is, the adipocyte-targeting sequence and the R9 peptide may also affect therapeutic efficiency on obesity. The weight ratio of the gene for treatment of obesity and obesity-induced metabolic syndromes to the adipocyte-targeting sequence and the R9 peptide may be 1:1 to 1:4, and more preferably 1:2. In a case where a weight content of the adipocyte-targeting sequence and the R9 peptide is less than the above range, there is a problem of being not bound well to the gene for treatment of obesity and obesity-induced metabolic syndromes. In a case where the weight content of the adipocyte-targeting sequence and the R9 peptide exceeds the above range, there is a problem that a complex size becomes too large so that influx into cells becomes impossible. Thus, both cases are not preferable.

As described above, the gene delivery complex according to the present disclosure comprises the adipocyte-targeting sequence (ATS) and the nine-arginine (R9) peptide, which is a structure (ATS-R9) in which the nine-arginine (R9) peptide is bound to the adipocyte-targeting sequence (ATS). As the adipocyte-targeting sequence (ATS), it is possible to use a known ATS [Nature Medicine, 2004 June]. Preferably, the ATS can consist of an amino acid sequence represented by SEQ ID NO: 2 below, but is not limited thereto.

SEQ ID NO: 2: CKGGRAKDC

As disclosed in Korean Patent Application No. 10-2013-0041402, which is a prior art document by the present inventors, the ATS-R9 binds to prohibitin in adipocytes. The prohibitin is an ATS receptor that is over-expressed in endothelial cells of blood vessels which support adipocytes and is present in both mature adipocytes and pre-adipocytes. The prohibitin plays an important role, in particular, in obesity, and its characteristics of being highly expressed in adipose tissue blood vessels and of migrating from the nucleus and mitochondria to the plasma membrane in differentiated adipocytes and being distributed in the plasma membrane as compared with adipocytes before differentiation suggests that the prohibitin can be a potential biomarker for obesity. In pre-adipocytes, the prohibitin is less distributed in the plasma membrane and is relatively highly distributed in the nucleus and mitochondria. However, in differentiated adipocytes, the prohibitin located in the nucleus and the mitochondria migrates to the plasma membrane and is highly expressed therein. That is, the prohibitin is over-expressed as differentiation proceeds. The ATS-R9 of the present disclosure is caused to be located in adipocytes via a prohibitin-mediated mechanism. In other words, the ATS plays an important role in targeting of adipocytes, and a degree of expression of a desired gene depends on an expression level of the prohibitin in adipocytes.

In particular, the prohibitin is over-expressed in mature adipocytes after differentiation as compared with adipocytes before differentiation. Thus, the ATS-R9 of the present disclosure has a function of directly targeting differentiated mature obese adipocytes. Specifically, for the ATS-R9 of the present disclosure, the most excellent targeting ability is exhibited for mature obese adipocytes which are at 9 to 11 days after initiation of differentiation. In the present disclosure, the terms "mature adipocytes" and "obese adipocytes" have the same meaning and are used interchangeably.

In addition, in the gene delivery complex according to the present disclosure, the nine-arginine (R9) peptide may have a structure of Cys-(D-R)9-Cys, and the ATS-R9 complex i) exhibits excellent efficiency in transfection and gene expression due to interactions with prohibitin in adipocytes; ii) improves transgene expression efficiency; iii) has a positive zeta potential value while binding to DNA to form a nano-sized complex, which makes it possible to pass through a cell membrane; and iv) has very low cytotoxicity.

Hereinafter, the present disclosure will be described in more detail with reference to the following examples. However, the following examples are intended to merely aid in understanding the present disclosure and are not intended to limit the scope of the present disclosure.

Cell culture, peptide preparation, cell staining, confocal microscopy observation, competition analysis, gel retardation analysis, zeta potential and size measurement, measurement of in vitro transfection efficiency, in vitro cytotoxicity analysis, induction of obesity in mouse models, in vivo fat targeting, differentiation of pre-adipocytes, evaluation of internalization ability into adipocytes, confirmation of adipocyte targeting ability depending on degree of differentiation, confirmation of prohibitin expression in various cells, measurement of physical and biological properties of produced oligo-peptoplexes, and the like were carried out by the same methods as described in Korean Patent Application No. 10-2013-0041402, the content of which is incorporated herein by reference in its entirety.

Example 1. Production of sh(FABP4+FABP5) Dual Plasmid Vector

In order to produce sh(FABP4+FABP5) dual plasmid vector, psiRNA-DUO (InvivoGen, USA), which is a dual RNA PolIII cassette vector for expression of two shRNAs, was used. Specific production processes are as follows.

A tube containing frozen plasmids was spun to precipitate DNA. In order to obtain a plasmid solution of 1 µg/µl, the obtained DNA was resuspended in 20 µl of sterilized water, and the resuspended plasmids were stored at −20° C. In order to increase yield, a plasmid amplification process was carried out by transforming E. coli with the resuspended plasmids.

Subsequently, the psiRNA-DUO plasmid was treated with restriction enzyme Bbs I (NEB, 2 units enzyme/µg plasmid DNA) and a large fragment (3180 bp) was eluted with 0.7% low melting point agarose gel. Then, the purified DNA fragment was diluted to obtain a solution of 0.1 µg/µl (Gus cassette). In addition, the psiRNA-DUO plasmid was treated with Acc 65I and Hind III (with NEB enzyme, NEBuffer 2+BSA) and a large fragment (3150 bp) was eluted using 0.7% low melting point agarose gel. Then, the purified DNA fragment was diluted to obtain a solution of 0.1 µg/µl (LacZ cassette).

In order to clone sh(FABP4+FABP5) into the psiRNA-DUO, a one-step process in which the psiRNA-DUO is treated simultaneously with Acc65 I, Hind III, and Bbs I, and ligation is performed together with two psiRNA-DUO sections (Hind III/Bbs I and Bbs I/Acc65 I) and two shRNA inserts, or a two-step process in which the first shRNA insert is cloned and then the remaining second shRNA insert is cloned was used. For details on the cloning process, reference can be made to the user's manual for psiRNA-DUO from InvivoGen (Catalog # ksirna4-gz3).

Example 2. Optimization of Content Ratio of sh(FABP4+FABP5) Plasmid and ATS-9R

Figure 1A:
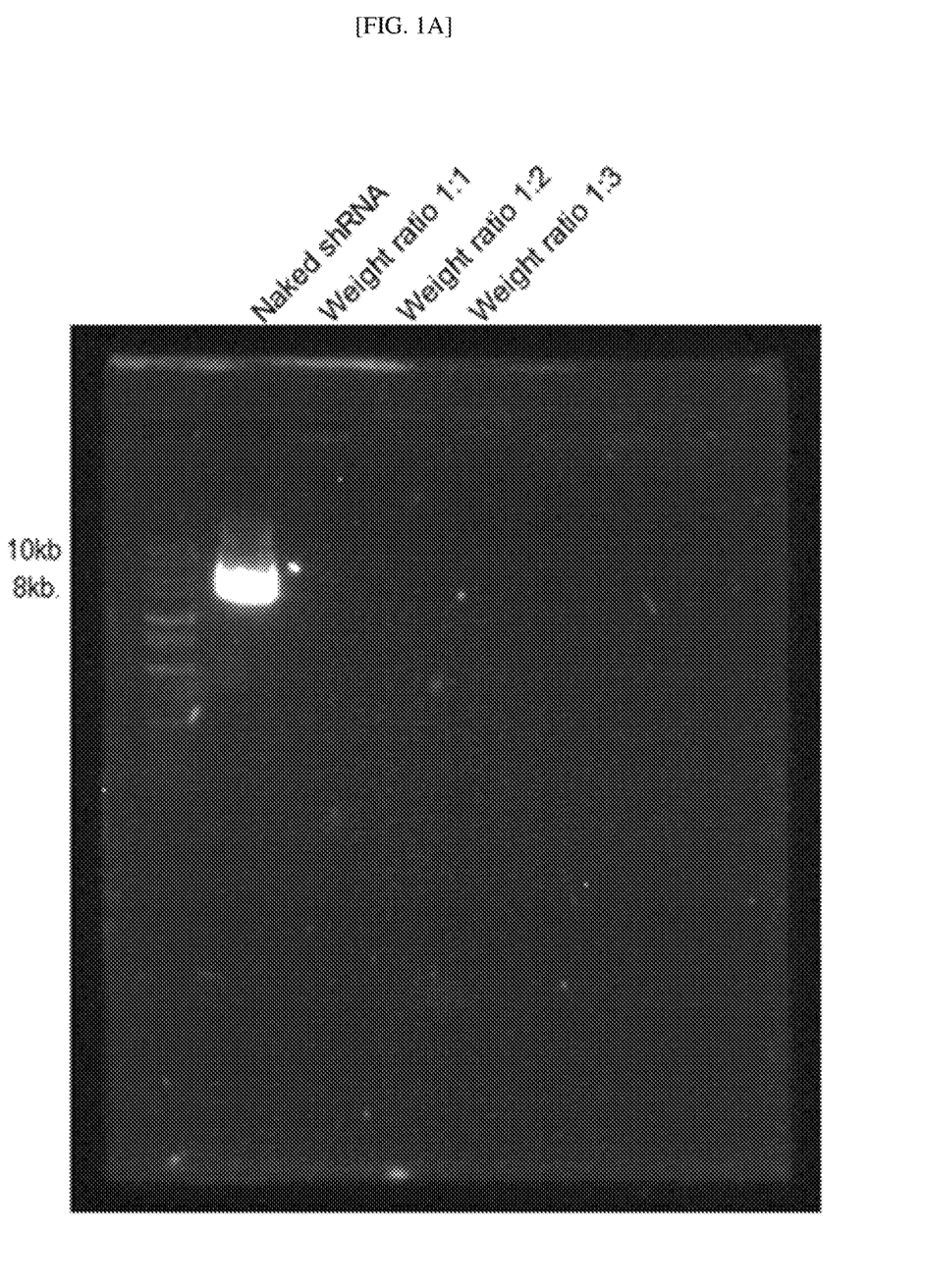
FIG. 1A is a view illustrating results of gel retardation analysis depending on a weight ratio of a sh(FABP4+FABP5) plasmid and ATS-9R.
Figure 1B:
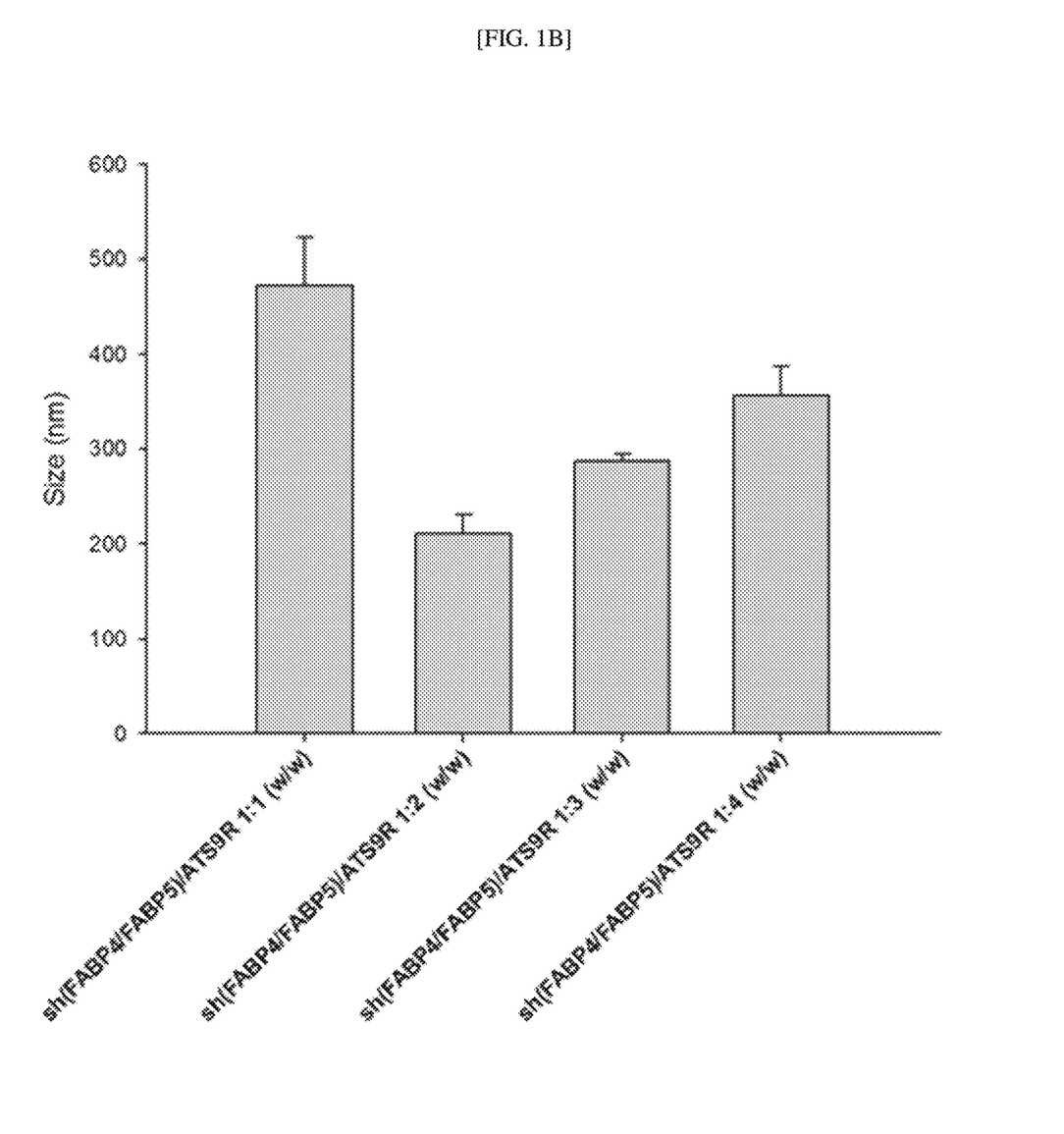
FIG. 1B is a view illustrating complex sizes depending on a weight ratio of a sh(FABP4+FABP5) plasmid and ATS-9R.

In order to optimize a content ratio of the sh(FABP4+FABP5) plasmid and the ATS-9R, a gel retardation assay was used. 1 µg of DNA, deionized water, and the ATS-9R were incubated at various weight ratios at room temperature for 30 minutes to produce oligo-peptoplexes. Average diameter and surface zeta potential of the oligo-peptoplexes were measured using a Zetasizer-Nano ZS (Malvern Instruments, UK) DLS. FIGS. 1A and 1B illustrate results of gel retardation analysis and complex sizes depending on a weight ratio of the sh(FABP4+FABP5) plasmid and the ATS-9R. Referring to FIG. 1B, it can be seen that an optimum size is obtained in a case where the weight ratio of the sh(FABP4+FABP5) plasmid to the ATS-9R is 1:2.

Figure 2A:
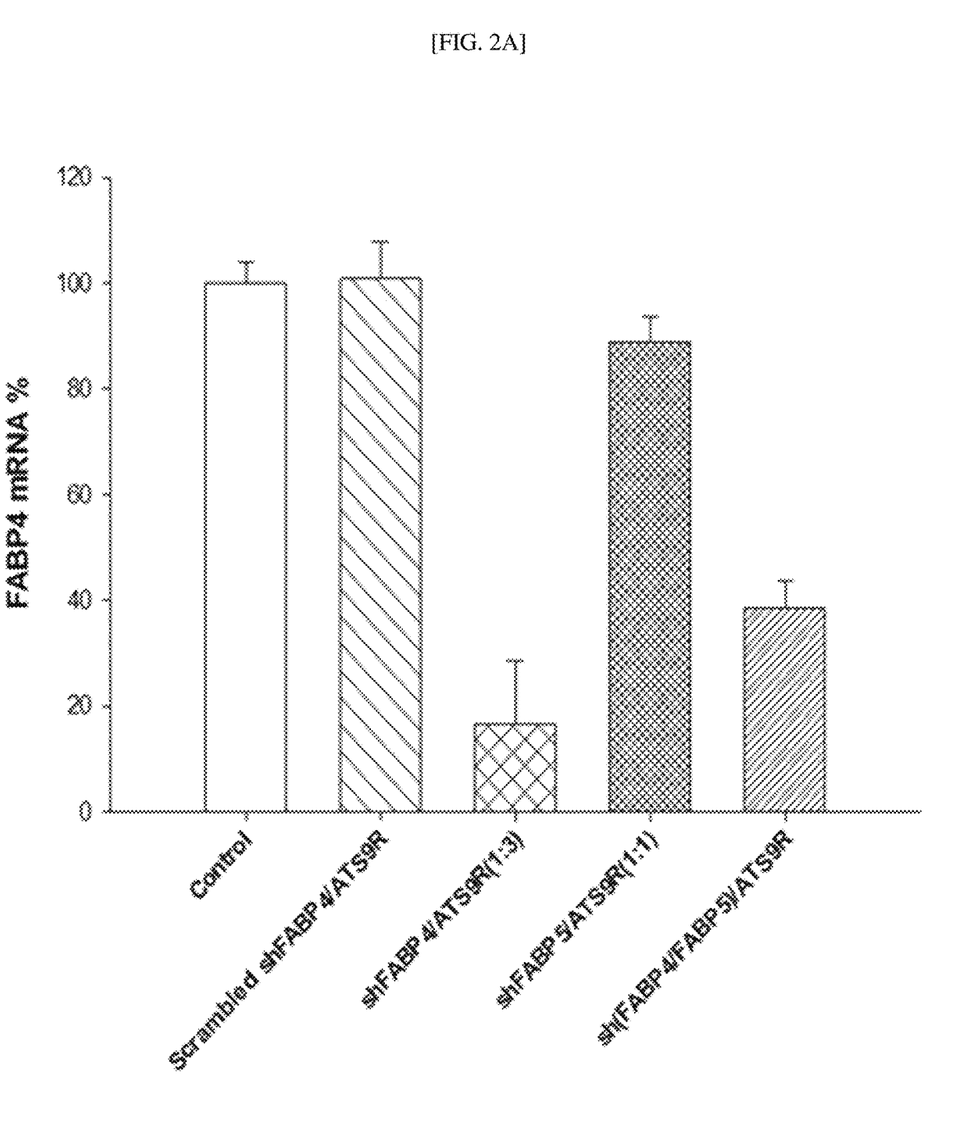
FIG. 2A is a graph illustrating results obtained by measuring a relative FABP4 mRNA level with respect to GAPDH through RT-PCR.
Figure 2B:
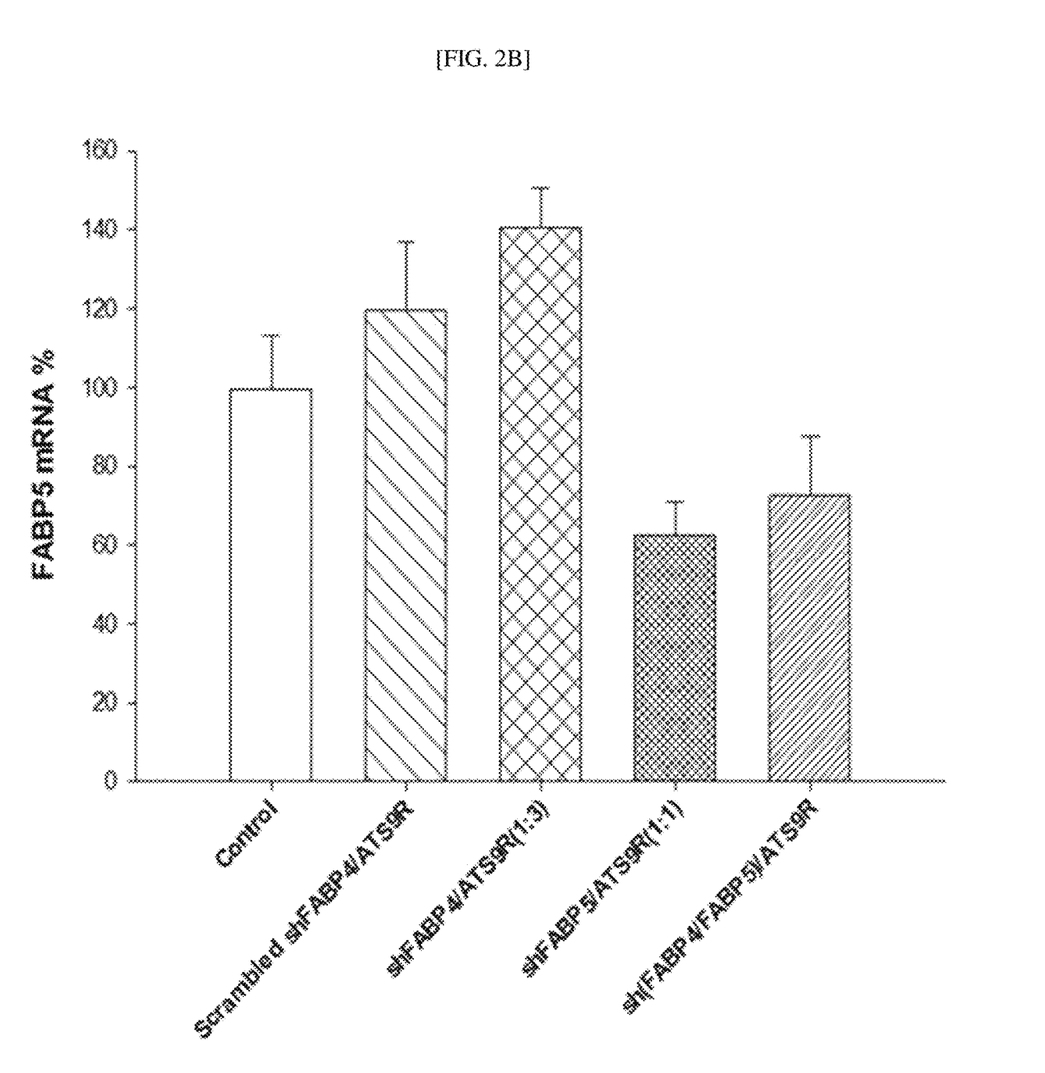
FIG. 2B is a graph illustrating results obtained by measuring a relative FABP5 mRNA level with respect to GAPDH through RT-PCR.

Example 3. Confirmation of Expression Levels of FABP4 and FABP5 in Adipocytes Transfected with Gene Delivery Complex According to Present Disclosure 3T3-L1 cells which are mouse-derived obese cells were differentiated into adipocytes, and then the differentiated adipocytes were treated with scrambled shFABP4+ATS9R, shFABP4+ATS9R, shFABP5+ATS9R, and sh(FABP4/FABP5)+ATS9R. After 48 hours, only RNA was isolated from the adipocytes using the RNeasy Lipid Tissue Mini Kit (Qiagen) and cDNA was synthesized. Then, relative mRNA levels of FABP4 and FABP5 with respect to GAPDH, which is an endogenous control, were measured through RT-PCR using a Cyber premix EX taq RT-PCR kit. FIGS. 2A and 2B illustrate the measurement results. Referring to FIGS. 2A and 2B, it can be confirmed that in a case where mature adipocytes were actually treated with the dual plasmid vector sh(FABP4/FABP5)+ATS9R through an in vitro experiment, mRNA amounts of FABP4 and FABP5 are decreased. In addition, it was confirmed that in a case where FABP4 is decreased, an mRNA amount of FABP5 is increased in the group (shFABP4+ATS9R). From this, it can be seen that FABP4 and FABP5 have to be simultaneously inhibited in order to achieve an optimal obesity-inhibiting therapeutic effect.

Example 4. Confirmation of Therapeutic Effect on Obesity of Gene Delivery Complex According to Present Disclosure Through Animal Experiments C57BL6/6N mice were fed a 60 kcal high-fat diet and bred for 2 to 3 months. Then, only mice weighing 45 g or higher were selected and were administered shFABP4/ATS9R, shFABP5/ATS9R, shFABP4/ATS9R+shFABP5/ATS9R, and sh(FABP4/FABP5)/ATS9R, which is the gene delivery complex according to the present disclosure, by IP injection twice a week.

Figure 3A:
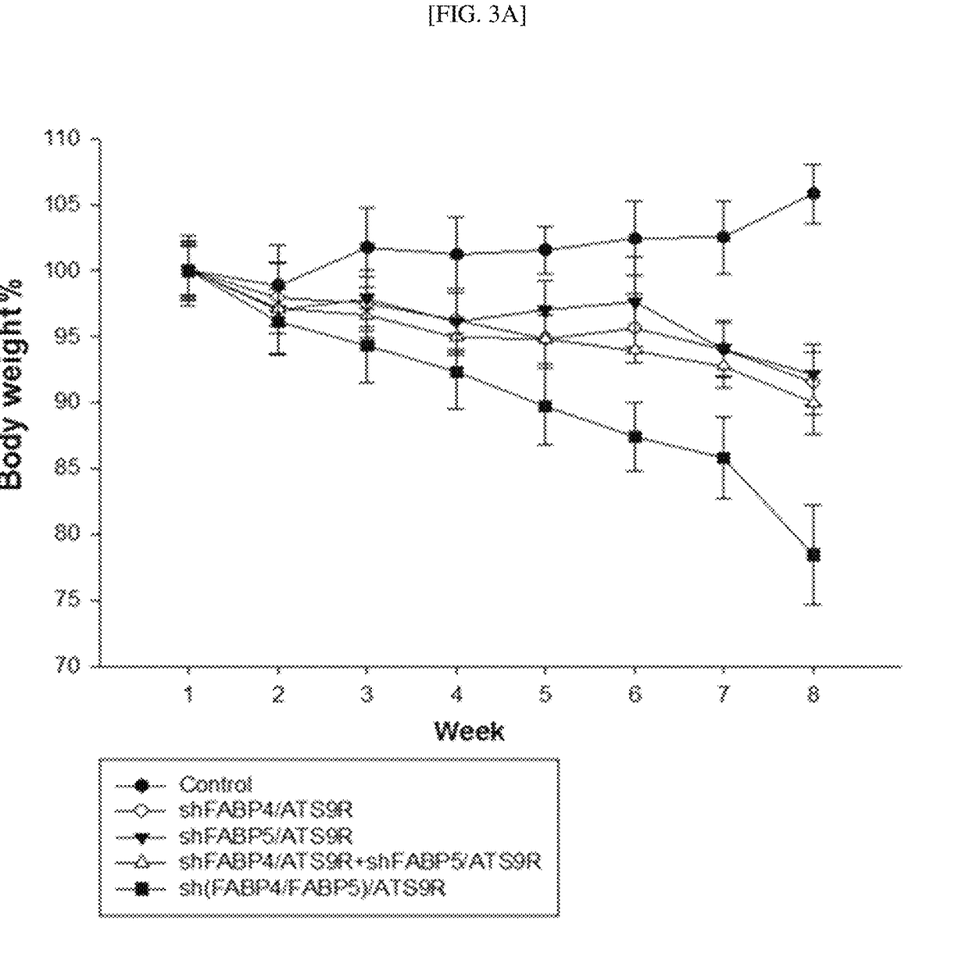
FIG. 3A is a graph illustrating results obtained by observing a change in body weight over time in each of administration groups which have been administered shFABP4/ATS9R, shFABP5/ATS9R, shFABP4/ATS9R+shFABP5/ATS9R, and sh(FABP4/FABP5)/ATS9R, respectively.

First, a change in body weight over time was observed for each of the administration groups. FIG. 3A illustrates a graph obtained by observing a body weight over time in each of the administration groups. Referring to FIG. 3A, it can be confirmed that a body weight loss effect of about 20% is exhibited in the group administered the gene delivery complex according to the present disclosure, whereas no significant body weight loss effect was exhibited in the other groups.

Figure 3B:
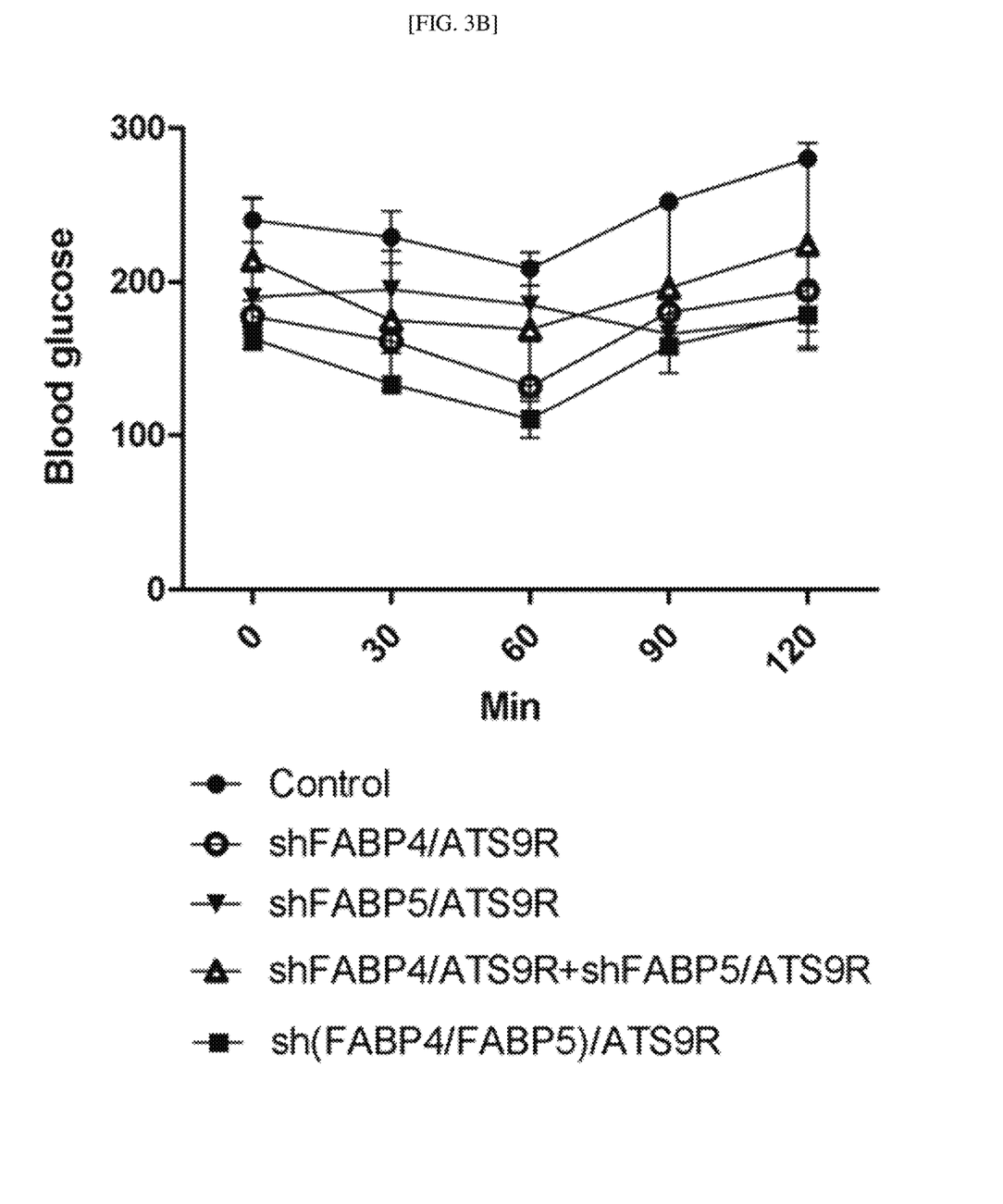
FIG. 3B is a graph illustrating results obtained by observing a change in blood glucose over time in each of administration groups which have been administered shFABP4/ATS9R, shFABP5/ATS9R, shFABP4/ATS9R+shFABP5/ATS9R, and sh(FABP4/FABP5)/ATS9R, respectively.

Next, ITT analysis was performed to observe a change in blood glucose over time in each of the administration groups. FIG. 3B illustrates a graph obtained by observing a change in blood glucose over time in each of the administration groups. Referring to FIG. 3B, it can be confirmed that a significant blood glucose-decreasing effect is exhibited in the group administered the gene delivery complex according to the present disclosure.

Figure 3C:
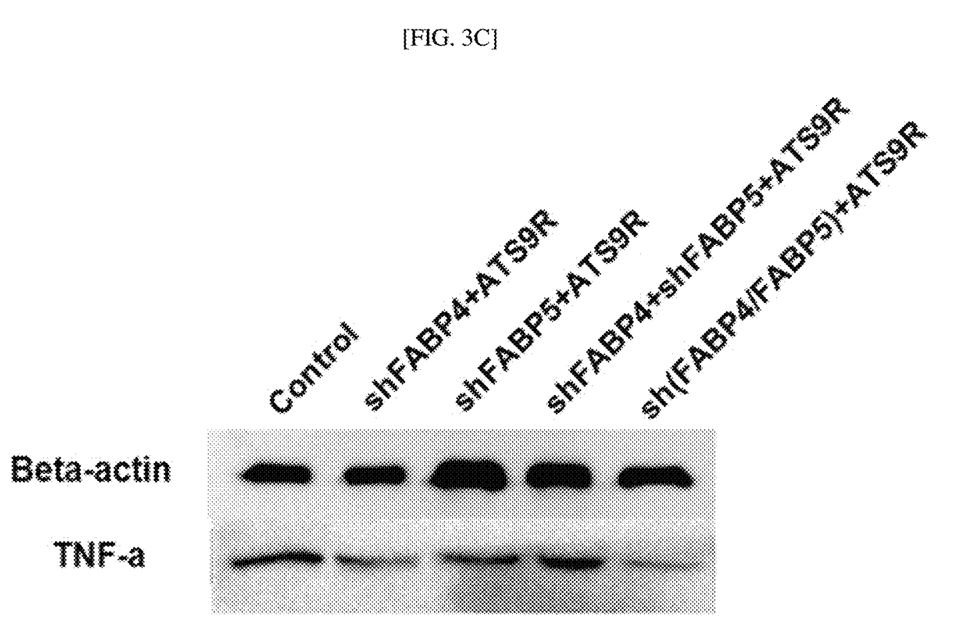
FIG. 3C is a view illustrating results obtained by extracting adipose tissue from each of administration groups which have been administered shFABP4/ATS9R, shFABP5/ATS9R, shFABP4/ATS9R+shFABP5/ATS9R, and sh(FABP4/FABP5)/ATS9R, respectively, and examining toxicity and inflammatory responses thereof through Western blotting.

Next, adipose tissue of mice was extracted, and toxicity and inflammatory responses thereof were examined through Western blotting. Specifically, for the adipose tissue, lysis was carried out in a RIPA buffer solution at pH 8.0 which contains 10 mM Tris-HCl, 1 mM EDTA, 140 mM NaCl, 0.1% SDS, 0.1% sodium deoxycholate, 1% Triton X-100, and a protease inhibitor cocktail, followed by incubation at 4° C. for 15 minutes. Then, centrifugation was carried out at 4° C. for 15 minutes at a speed of 14,000 g, and a supernatant was used as a sample. The sample was electrophoresed by SDS-PAGE, transferred to a polyvinylidene difluoride (PVDF) membrane, and subjected to Western blotting. FIG. 3C illustrates results of Western blotting. Referring to FIG. 3C, it can be seen that TNF-α, which is an inflammation marker, is decreased in the group treated with sh(FABP4/FABP5)+ATS9R as compared with the other groups.

Figure 3D:
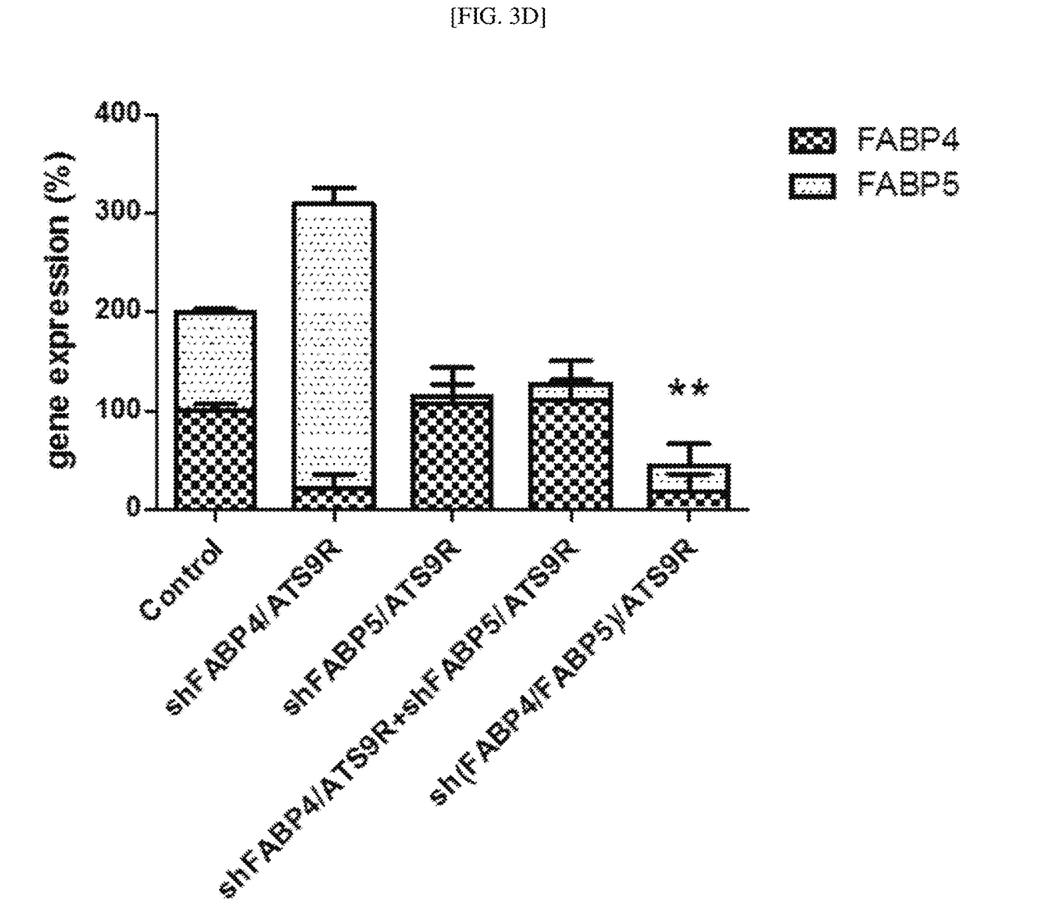
FIG. 3D is a graph illustrating results obtained by confirming expression rates (%) of the FABP4 and FABP5 genes in adipose tissue of each of administration groups which have been administered shFABP4/ATS9R, shFABP5/ATS9R, shFABP4/ATS9R+shFABP5/ATS9R, and sh(FABP4/FABP5)/ATS9R, respectively.

Next, expression rates (%) of the FABP4 and FABP5 genes in adipose tissue of mice were observed in each of the administration groups. FIG. 3D illustrates gene expression rate (%) results for the respective genes. Referring to FIG. 3D, it can be seen that the expression rates of the FABP4 and FABP5 genes were significantly decreased in the group treated with sh(FABP4/FABP5)+ATS9R as compared with the other groups.

INDUSTRIAL APPLICABILITY

The gene delivery complex according to the present disclosure is constructed so as to be capable of delivering the FABP4 gene and the FABP5 gene, which are obesity-related therapeutic genes, specifically into adipocytes while at the same time achieving simultaneous inhibition of these genes. In this manner, an excellent therapeutic effect on obesity can be achieved without cytotoxicity. Thus, the gene delivery complex according to the present disclosure is expected to be usefully used in gene therapy techniques for treating obesity and obesity-induced metabolic syndromes.

The invention claimed is:

1. A gene delivery complex, comprising:
   an adipocyte-targeting sequence;
   a nine-arginine (R9) peptide; and
   a dual plasmid vector comprising a shRNA for treatment of obesity and obesity-induced metabolic syndromes,
   wherein the shRNA for treatment of obesity and obesity-induced metabolic syndromes is a nucleotide sequence inhibiting expression of a FABP4 gene and a FABP5 gene, and the plasmid vector comprises the nucleotide sequence of SEQ ID NO: 1.

2. The gene delivery complex of claim 1, wherein a weight ratio of the shRNA for treatment of obesity and obesity-induced metabolic syndromes to the adipocyte-targeting sequence and the R9 peptide is 1:1 to 1:4.

3. The gene delivery complex of claim 1, wherein a weight ratio of the shRNA for treatment of obesity and obesity-induced metabolic syndromes to the adipocyte-targeting sequence and the R9 peptide is 1:2.

4. The gene delivery complex of claim 1, wherein the adipocyte-targeting sequence comprises the amino sequence of SEQ ID NO: 2.

5. The gene delivery complex of claim 1, wherein the nine-arginine (R9) peptide has a structure of Cys-(D-R)9-Cys.

6. The gene delivery complex of claim 1, wherein the adipocyte is a differentiated mature obese adipocyte.

* * * * *